United States Patent [19]

Ohsumi et al.

[11] Patent Number: 5,367,111
[45] Date of Patent: Nov. 22, 1994

[54] HYBRID PLANTS OF ONION AND GARLIC OR CHINESE CHIVE AND METHOD FOR BREEDING AND PROPAGATING THE SAME

[75] Inventors: Chieko Ohsumi, Kawasaki; Takahisa Hayashi, Uji, both of Japan

[73] Assignee: Ajinomoto Co., Inc., Tokyo, Japan

[21] Appl. No.: 616,509

[22] Filed: Nov. 21, 1990

[30] Foreign Application Priority Data

Nov. 21, 1989 [JP] Japan ................................ 1-300770
Mar. 5, 1990 [JP] Japan ................................ 2-52940
Oct. 19, 1990 [JP] Japan ................................ 2-281086

[51] Int. Cl.$^5$ .......................... A01H 5/00; A01H 1/00; C12N 5/00
[52] U.S. Cl. ........................... 800/200; 800/DIG. 59; 47/58; 47/DIG. 1; 435/240.4; 435/240.45
[58] Field of Search ................ 800/200, DIG. 59; 47/58, DIG. 1; 435/240.4, 240.45

[56] References Cited

U.S. PATENT DOCUMENTS 4,672,035 6/1987 Davidonis et al. ................ 435/240

FOREIGN PATENT DOCUMENTS 0385296 9/1990 European Pat. Off. .

OTHER PUBLICATIONS

Gonzalez et al., Plant Breeding, 98:318–322, 1987.
Dolezel et al., Z. Pflanzanzunchtg, 85:177–184, 1980.
Fukuda et al., "Lecture Summary of Nippon Shokubutsu Soshiki Baiyo Gakkai Taikai" (Jul. 18, 1989) (Applicants' Translation thereof).
Havey, Theor. Appl. Genet., 81:752–757, 1981.
Rabinowitch and Brewster, eds., Botany, Physiology and Genetics, vol. 1, Onions and Allied Crops, CRC Press, Inc., Boca Raton, Fla., USA, ch. 1, pp. 1–26, 1990.
Novak, F. J. et al (1986) Handbook of Plant Cell Culture, vol. 4 MacMillan Publ. pp. 419–456.

Primary Examiner—David T. Fox
Assistant Examiner—E. F. McElwain
Attorney, Agent, or Firm—Pennie & Edmonds

[57] ABSTRACT

Hybrids of onion and garlic or Chinese chive are obtained by culturing the ovule-embryo after fertilization of the male (e.g. garlic pollen) and female (e.g. onion egg cell) gametes. The hybrids have the useful characteristics of both species and can be propagated.

11 Claims, 4 Drawing Sheets

HYBRID PLANTS OF ONION AND GARLIC OR CHINESE CHIVE AND METHOD FOR BREEDING AND PROPAGATING THE SAME

FIELD OF THE INVENTION

This invention relates to a hybrid cell and a hybrid plant obtained by crossing an onion with garlic or a Chinese chive, and to a method for breeding and propagating the same.

BACKGROUND OF THE INVENTION

Much progress in plant improvement has been made by seed propagation involving the repeated process of collecting seeds from plants that look best in a field. However, a conventional seed propagation method has not been successfully applied to vegetatively propagative plants, e.g., garlic. The improvement of such plants has been made by repetitive selection of propagules, which requires a number of years. In addition, the conventional breeding method based on sexual reproduction is restricted only to those between closely related plants, although there are many cases in which seeds cannot be obtained.

Recently, seed propagative garlic has been found and sexual reproduction of seed-fertile clones has become feasible. However, there has been no report on a new cultivar obtained by seed propagation, yet.

On the other hand, a cell fusion technique was developed to bypass "the barrier of seed propagation" which set a limit to the conventional breeding method. Although the cell fusion technique is applicable to hybridization of seed-sterile plants, the technique is known to cause heritable alteration such as changes in chromosome number during plant regeneration. Plants belonging to the genus *Allium*, such as onion, garlic and Chinese chive are generally difficult to form somatic embryos, and the fused cell is also difficult to regenerate. In addition, it has been reported on the stability of the fused cell that either one of the chromosome sets of the cell is likely to be lost during growing into a plantlet.

There has been no report that the hybrid plants of an onion and a Chinese chive can be made by the conventional crossbreeding method or a cell fusion technique.

SUMMARY OF THE INVENTION

It is an object of the invention to provide a hybrid of an onion and garlic or a hybrid of an onion and a Chinese chive and a method for the production of the hybrid which has useful characteristics from both plants.

The present inventors have crossed an onion with garlic or a Chinese chive, to develop their hybrid plants, and cultured the ovule removed from the standing plant after hybridization in a plant culture medium. A hybrid embryo, capable of germination, differentiation and growth was successfully grown in the culture medium and the hybrid plant having the traits of both plants can be obtained.

The present invention relates to a hybrid embryo which is obtained from hybridization of an onion and garlic or a Chinese chive and is capable of germination, differentiation and growth, and to a hybrid cell and a hybrid secondary embryo derived from the hybrid embryo as well as hybrid plants obtained from culturing these embryos. The invention also relates to a method of breeding and propagating a hybrid embryo, a hybrid cell, and a hybrid secondary embryo and a hybrid plant.

As an onion (*Allium cepa* L.) used for hybridization of the invention, any onion may be used as far as its pollen or egg cell is fertile. For example, commonly cultivated onion cultivars such as Sapporo-ki, Senshu-ki, and Shonan red may be used.

Any garlic (*Allium sativum* L.) and any Chinese chive (Allium *tuberosum* Rottier) may be used as far as their pollen and egg cells are fertile.

A hybrid cell, a hybrid embryo, a hybrid secondary embryo and a hybrid plant of the present invention are defined as follows.

A hybrid cell is intended to include all the cells ranging from a single-celled zygote to cells constituting a hybrid plant. Also included is callus which is induced from the hybrid plant tissues at every stage in development. The nucleus of these hybrid cells must contain at least one chromosome each from both parental species.

A hybrid embryo is intended to mean an embryo which is developed from the hybrid cell, and capable of germination, differentiation, and growth, resulting in a hybrid plant. The color of the hybrid embryo is white to green. Its size is 1-5 mm.

A hybrid secondary embryo is intended to mean the one which is obtained via the hybrid embryo and has the same characteristics as those of the hybrid embryo.

A hybrid plant is intended to mean a juvenile and an adult plants derived from any of the hybrid cell, the hybrid embryo and the hybrid secondary embryo.

In the description which follows, methods according to the present invention are described in detail.

a. Fertilization

In hybridization of an onion and garlic or a Chinese chive, the pistils of any of the above plants may be used. Although the pistils may be cultured in a culture medium, it is preferred to use the pistil as it remains on a standing mother plant in order to ensure the growth. When, the standing plant is used for hybridization, extreme care should be taken to avoid self-pollination. To prevent self-pollination, all the anthers are excised or coated with viscous substances or plastic immediately after the flowering. Alternatively, a male sterile line may be used. Plants belonging to the genus *Allium* in general are protandrous so that there is no possibility of self-pollination if excision is performed before the flowering. Accordingly, it is highly probable that the resulting embryo is a hybrid. Pollination may be carried out according to conventional methods, e.g. using a writing brush to coat pistils with pollen. Pollen germinates on the stigma, and a pollen tube grows down until it reaches the embryosac where fertilization occurs. The zygote may be a hybrid cell with embryogenic and dividing ability.

b. Ovule culture

After fertilization, an ovule containing the zygote is cultured in a plant culture medium. The transfer of the ovule to a medium may be done within one month after fertilization. Prior to removal of the ovule from the ovary, it is preferred to sterilize the flower. The sterilization may be carried out according to conventional methods, e.g., immersion of the flower into 70% ethanol solution or hypochloric acid solution.

As a plant culture medium, any medium can be used as far as it may be used for plant culture. For example, a medium prepared by adding 5 to 100 g/l of sucrose, glucose, or fructose as a carbon source to an inorganic salt medium such as Murashige & Skoog's medium, Linsmaier & Skoog's medium, White's medium, Gamborg's medium or a medium prepared by modifying any one of the above media can be used. It is preferred that the above medium is used as a solid medium prepared by adding vitamins, inositol and, if necessary, plant hormones, Casamino acid and amino acids and then solidifying with agar or gellan gum. For example, satisfactory results can be obtained by using a medium prepared by selectively adding thereto 1 to 1,000 mg/l of inositol, 0.001 to 5 mg/l of nicotinic acid, 0.01 to 1 mg/l of thiamine hydrochloride, 0.01 to 1 mg/l of pyridoxal hydrochloride, 1 to 1,000 mg/l of Casamino acid, 0.01 to 10 mg/l of glycine, 1 to 1,000 mg/l of arginine, 1 to 1,000 mg/l of glutamine and 1 to 1,000 mg/l of alanine, and auxin and cytokinin as plant hormones. The culturing temperature may be 20° to 30° C. Preferable results may be attained by culturing the ovule at room temperature under the artificial light.

c. Embyro culture

After several weeks, a hybrid embryo, specifically an embryo or an embryoid is removed from the aforementioned cultured ovule and further cultured in an embryo culture medium. This medium may have the same composition as the above medium for the ovule culture. Advantageous results may be obtained by lowering the concentration of sugar used as a carbon source.

Other culture conditions may be similar to those of the ovule culture. The embryo or the embryoid is germinated under the above conditions to grow into a plantlet having leaves and roots. After acclimation, the plantlet is potted, and an adult hybrid plant can be obtained.

Alternatively, when the above hybrid embryo is cultured in an ovule culture medium or an embryo culture medium, preferably in a medium prepared by adding 0.01 to 2.0 mg/l each of auxin and cytokinin to an embryo culture medium, a hybrid cell cluster callus can be obtained. A callus can be subcultured according to conventional methods and can be regenerated into a hybrid plant by allowing callus to form an adventitious embryo or an adventitious bud and subsequently an adventitious root.

Furthermore, a hybrid secondary embryo can be induced from an hybrid embryo. For example, a hybrid secondary embryo can be induced by culturing a hybrid embryo in a medium prepared by adding 0.5 mg/l each of 1-naphthaleneacetic acid and 6-benzyladenine as plant hormones under the artificial light. 1-Naphthaleneacetic acid may be replaced by 2,4-D or 3-indolebutyric acid, and benzyladenine may be replaced by kinetin. The induced hybrid secondary embryo is germinated under the same culture conditions as described above in the hybrid embryo culture, and grows into a plantlet having leaves and roots. After acclimation, the plantlet is potted, and an adult hybrid plant can be obtained.

Single hybrid cells can be isolated by treating the hybrid embryo, the hybrid secondary embryo or the hybrid cell callus with, for example, cellulase or pectinase.

Alternatively, the single hybrid cell may also be isolated by culturing a hybrid cell callus in an amino acid medium. The hybrid cells exist in Basic Research Laboratory, Central Research Laboratories, Ajinomoto Co., (1-1,Suzuki-cho, Kawasaki-ku, Kawasaki-210 JAPAN).

Hereinafter, a method for propagating the hybrid plant is described in detail.

In propagation of the hybrid plants, the complete characteristics of the hybrid plants can be maintained by vegetative propagation. Specifically, the hybrid plants can be propagated by cultivating cloves or aerial bulbils thereof. As a soil to be planted, a weakly acidic field (pH 5.5 or higher) is suitable. The hybrid plants may be planted either densely or sparsely. Around the middle of September, compost lime and fused magnesium phosphate may be applied to the field. The field should be plowed, tilled, supplied with a basal fertilizer and then ridged. The ridge may be a single or double row-planting ridge, or a wide ridge comprising 3 to 4 rows. A level ridge is preferred for upland field, while a high ridge is preferred for paddy field. Planting is usually carried out from the beginning of October to the middle of November. To prevent disease injuries, it is recommended to employ a disinfection method in which the hybrid plant are immersed in a 1,000-fold dilution of Benlate wettable powders for 30 minutes. For protection of the hybrid plant from root mites, it is recommended to immerse the hybrid plant in a 3,000-fold dilution of Sumithion emulsifiable concentrate for 30 minutes. From the middle of February to the beginning of April, the first top dressing is applied. The cloves of the hybrid plants can be harvested from May to July. Alternatively, aerial bulbils formed at the tip of the cloves which have passed the edible time can be collected.

In addition, certain hybrid plants may have fertility depending on the selection of parental plants. In such a case, the hybrid plant can be propagated by the seed. Plants of the genus *Allium* are protandrous and are not readily self-pollinated. In order to get self-pollination of *Allium* species, the flowers of the plant should be covered with bags in which flies are set free. A conventional method can be used to collect the seeds. The collected seeds can be germinated in the same manner as those of an onion, a Chinese chive and garlic. The percentage of germination may be improved by the treatment with 1 to 100 ppm of gibberellin. The plantlet germinated from the seed can be cultivated as described as above.

Alternatively, a clonal propagation method using a tissue culture technique can also be employed. In this method, the growing points of cloves, shoots or roots are removed aseptically and then cultured in a basal medium for tissue culture. For example, a medium prepared by adding 5 to 100 g/l each of sucrose, glucose, fructose, etc, as a carbon source to Murashige & Skoog's medium, Linsmaier & Skoog's medium, White's medium, Gamborg's medium, Heller's medium or a medium prepared by modifying any of the above media can be used. Satisfactory results can be obtained by using a medium prepared by selectively adding 1 to 1,000 mg/l of inositol, 0.001 to 5 mg/l of nicotinic acid, 0.01 to mg/l of thiamine hydrochloride, 0.01 to 1 mg/l of pyridoxal and 0.01 to 10 mg/l of glycine and further adding auxin and cytokinin as plant growth regulators to the above medium. The culture temperature may be 20° to 30° C. Generally, satisfactory results can be obtained by culturing at room temperature under the artificial light. After forming a multigerminated shoot body or vegetative shoots, it is transplanted to a rooting medium to grow into a plantlet. The plantlet is acclimated and then potted. The potted plantlet is grown in a greenhouse for 2 weeks to 1 month and then transplanted to a field. The time for transplantation is usually from the end of September to December. The transplanted plantlet can be grown as described above.

All the hybrid plants obtained according to the above-mentioned methods are characterized by possessing at least one genetic trait from each of their parent. The nature of hybrids can be determined by the morphological observation of leaves, stems, and flowers, or the chromosome numbers and the isozyme pattern of the plants. The genetic characteristics in the cytoplasm of the hybrid plant are inherited exclusively from the mother.

Most of genetic characteristics are expressed in the developmental stage after embryogenesis. Such genetic characteristics specifically include the constituent of secondary metabolites, the plant type, cold resistance, disease resistance, and fertility of the plant. For example, 1 g of leaves from onion×garlic hybrid plant contains 0.1 to 300 mg of propenyl cysteine sulfoxide as a constituent of an onion, 0.1 to 300 mg of alliin (allyl cysteine sulfoxide) as a constituent of a garlic and 0.05 to 300 mg of methyl cysteine sulfoxide as a constituent of both the onion and garlic. Based on the parental genetic properties, the characteristics of an onion×garlic hybrid plant can be manipulated to express the plant type of the onion plus the constituents, cold resistance, and disease resistance of garlic. Similarly, characteristics of onion×Chinese chive hybrid plant can be manipulated to express genetic properties of the onion plus the parthenogenetic nature of the Chinese chive. The genetic properties of a hybrid plant depend upon those of its parent as described above. The traits of the hybrid plant can be theoretically predetermined if those of the parents are known. In addition, the offsprings of the hybrid plant stably inherit the parental genetic properties and do not lose any traits of its parents.

The chromosomes of the hybrid plant may be identified by rDNA analysis. The genetic properties in the cytoplasm of the hybrid plant may be determined by analyzing DNA of chloroplasts or mitochondria. These methods are described in detail in the following literatures:

Gleba and Sytnik, Protoplast Fusion, ed. R. Shoeman (Springer-Verlag, 1984)

Uchimiya et al, Theor. Appl. Genet., 64, pp. 117~118 (1983)

THE EFFECT OF THE INVENTION

Figure 1:
FIG. 1 illustrates the hybrid embryo obtained by hybridizing an onion and garlic at the cylindrical embryo stage of development.

The advantageous properties of an onion, garlic and a Chinese chive belonging to the genus *Allium* have not been mutually utilized, by the above plants. According to the present invention, the useful characteristics of the above plants can be utilized synergistically as a form of hybrids such as an onion×garlic hybrid and an onion×Chinese chive hybrid. Hybrid formation between the above plants has become possible for the first time by the present invention.

Specifically, useful characteristics which may be mentioned include a constituent propenyl cysteine sulfoxide which is a flavor precursor, seed fertility, disease resistance and early maturation in the case of an onion, and a constituent alliin which is a flavor precursor, low seed fertility, and slow maturation in the case of garlic. The invention provides a method for the production of a hybrid which bears at least one characteristic of each of the parents.

One of the distinguishing features of the present invention is that the hybrid plant can be grown from the hybrid embryo formed by fertilization of the male (e.g. garlic pollen) and female (e.g. egg cell of an onion) gameres. The parental plant is diploid (2n), and its gameres are haploid (1n). The haploid male and female gameres are fertilized to form the hybrid zygote which may become the hybrid embryo. The hybrid embryo may continue to grow only when it is artificially cultured by the method of the present invention, and otherwise the embryo dies. The invention provides a method to help the embryo develop into the subsequent stages.

If a protoplast fusion technique is used for *Allium* species, the fused cell must be manipulated to form an adventitious bud and then to form an adventitious root since callus from plants belonging to the genus *Allium* have less ability of adventitious embryogenesis. In the present invention on the other hand, one may simply facilitate germination of the embryo, because a hybrid embryo can be obtained in the present invention. Once a zygote capable of division is obtained in the present invention, the stable growth of the zygote into the subsequent stages in development is ensured. A protoplast fusion technique is nothing like the method of the invention for maintaining genetic stability of the hybrid embryo and enabling it to develop into the plantlet. In addition, the hybrid plant of the present invention can be potted within a very short period of time, e.g. two months after fertilization. Furthermore, the hybrid plant itself can also be used as a mother plant for further breeding. The chromosomes of the hybrid cell can be polyploidized by colchicine treatment. The hybrid plants which are fertile can be subjected to backcrossing or crossing with any of the species in the genus *Allium*.

Another feature of the present invention is that either fertile pollen or fertile egg cell may be used in the case garlic is used. The garlic need not necessarily be derived from a seed-fertile line, as long as either its pollen or egg cell is fertile. According to the method of the invention, either pollen from an onion or from garlic can be used for pollination. Therefore, the egg cell of an onion may be used for pollen of garlic, and vice versa.

EXAMPLES

The following Examples are intended to illustrate but not to limit the invention.

EXAMPLE 1

Hybrid of an Onion and Garlic

Just after the flowering of the onion (Sapporo-ki K1), anthers thereof were removed carefully with forceps. The flower was then covered with a bag in order to prevent contamination of other pollen. After three days, the matured stigma of the onion was pollinated by pollen of garlic. The flower was harvested three days after pollination. The flower was sterilized in 75% ethanol solution for 1 minute and subsequently in 10% antiformin for 1 minute, and then washed twice with sterile water. Then, the ovule was asceptically removed from the flower under a microscope, placed on a medium and cultured at 25° C. for 16 hours under artificial light. The medium used was a solid medium prepared by adding 80 g/l of sucrose, 100 mg/l of inositol, 100 mg/l of Casamino acid and 0.01 mg/l of indole acetic acid to an inorganic salt medium of Gamborg's B-5 and solidifying with agar. The hybrid embryo developed from the ovule was transplanted to the same medium as described above except for decreasing the concentration of sucrose to 20 g/l, and then cultured in the same manner as described above. The hybrid embryo was acclimated when it developed the second leaf and generated roots. The plantlet was then transplanted to a pot to grow into an adult hybrid plant.

Figure 2:
FIG. 2 illustrates the transplanted hybrid embryo of an onion and garlic in an embryo culture medium and germination of the embryo.
Figure 3:
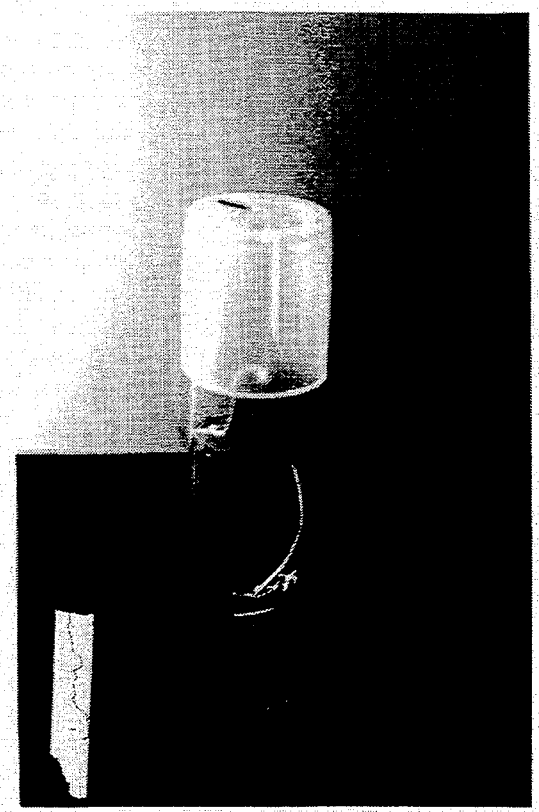
FIG. 3 illustrates that the hybrid embryo of an onion and garlic generated leaves and roots.
Figure 4:
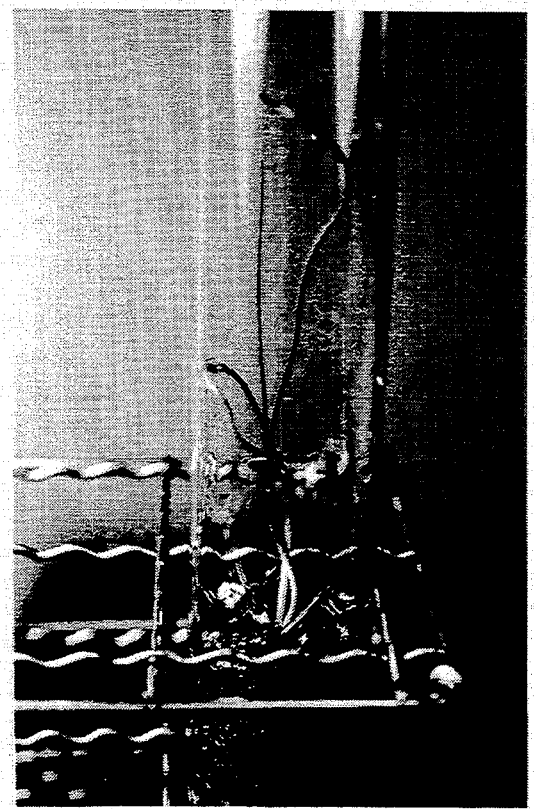
FIG. 4 shows the hybrid plant of an onion and garlic, at the three leaf stage, acclimated in vermiculite in a test tube.

The growth of the hybrid is shown in FIG. 1-4. FIG. 1 shows the hybrid embryo developed from an ovule and at the cylindrical embryo stage in development. FIG. 2 shows the transplanted hybrid embryo in an embryo culture medium and rootings of the embryo. FIG. 3 shows that the hybrid embryo generated leaves and roots. FIG. 4 shows the hybrid plant acclimated in vermiculite in a test tube. The hybrid plant was in the three-leaf stage.

The nature of hybrid plant was tested as follows. The leaf shape of the hybrid plant was an intermediate between the onion and garlic, and the leaf arrangement of the hybrid plant was that of garlic. An onion has cylindrical and hollow leaves. The leaf arrangement is not alternate, but the leaves grow out from the bottom of the shoot, while garlic has flat leaves whose blade is folded toward the midrib. The leaf arrangement is alternate. The leaves grow out from the upper part of the shoot. The hybrid plant had flat and hollow leaves. The leaf arrangement was alternate and the leaves grew out from the upper part of the shoot.

The color of garlic shoot is purple and that of onion shoots is yellow. The color of the hybrid shoot was purple, characteristic of garlic.

In addition, it is found by constituent analysis that the flavor precursors of the hybrid plant contained those of an onion and garlic.

The constituent analysis of the flavor precursors was carried out in the following manner. Approximately 20 mg (fresh weight) each of leaves of the hybrid plant, the onion (Sapporo-ki K1) and garlic was homogenized in 0.5 ml of a mixture of methanol, chloroform and water (12:5:3) in order to prevent the amino acids (flavor precursor) from decomposing by alliinase. The mixture was extracted with water, and the aqueous layer containing the precursors was analyzed by high performance liquid chromatography. Samples were separated and identified using an amino acid analysis column (Waters, Inc.; No. 80002, strong cation exchange column) under conventional chromatographic conditions. Amino acids fractionated were automatically reacted with orthophthalaldehyde and analyzed using a spectrophotofluorometer F1000 (Hitachi, Ltd.). The respective contents of propenyl cysteine sulfoxide, alliin and methyl cysteine sulfoxide which are the precursors of the characteristic flavor and tastes of the onion and garlic are given in Table 1. Since the hybrid plant contained both propenylcysteine sulfoxide and alliin which are respectively characteristic of an onion and garlic, the plant has been proved to be a hybrid.

TABLE 1

| | Content of Flavor Precursor mg/g (fresh weight) | | |
|---|---|---|---|
| | MCSO | Alliin | ProCSO |
| Hybrid Plant | 3.14 | 2.11 | 11.65 |
| Onion | 0.16 | — | 6.35 |
| Garlic | 4.1 | 4.63 | — |

MCSO: methyl cysteine sulfoxide
ProCSO: propenyl cysteine sulfoxide

Sixteen chromosomes were observed in the cell of the hybrid plant by chromosome analysis. The chromosome analysis was carried out in the following manner. Using a sharp razor blade, 5-10 mm sections from the root apex of the hybrid plant were cut off. The sections were pretreated with 0.05% colchicine solution. After thoroughly washing, the sections were fixed with an acetic acid-alcohol mixture (glacial acetic acid:ethyl alcohol=1:3) at 10° C. After fixation, the sections were sequentially immersed for 5 minutes each at room temperature in each of 70, 30 and 15% ethyl alcohol solutions and, then twice in distilled water. After washing with water, the sections were immersed in 1N hydrochloric acid solution at room temperature for 3 minutes and subsequently treated with preheated (60° C.) 1N hydrochloric acid solution for 8 minutes. The sections were cooled to room temperature as quickly as possible, then washed 3 times with water for 5 minutes each. The sections were drained and then immersed in Schiff's reagent (staining) for 1 hour at room temperature. Immediately after staining the sections were immersed in a solution containing 5 ml of 1N hydrochloric acid, 5 ml of 10% sodium bisulfite, and 100 ml of distilled water to wash out the unreacted reagent. Then, the strongly stained part at the top of the specimen was placed on a slide glass, onto which 1 or 2 drops of a 45% acetic acid solution were added and a cover glass was placed on it. After spreading the tissue to a thin layer according to a squash method, the cell was observed using an optical microscope (1,000×magnification) to count the number of chromosomes.

Esterase of the hybrid plant was tested for the isozyme pattern. Two hundred mg each of the leaves of the hybrid plant, the parental onion and parental garlic was homogenized in 1 ml of 0.05M phosphate buffer (pH 6.7), followed by centrifugation. Each supernatant was placed on 5.3% T and 5% C acrylamide gel (pI 3-10 BIOLYTE) and subjected to isoelectric focusing. Esterase activities were stained with 0.1% Fast Blue RR salt and 0.33% α-Naphthyl Acetate. Five bands for the onion and four bands for the garlic were found to have a different mobility from each other, and all the nine bands were found for the hybrid plant.

EXAMPLE 2

Hybrid of an Onion and a Chinese Chive

Just after the flowering of the onion (Sapporo-ki K1), anthers thereof were removed carefully with forceps. Then, the flower was covered with a bag in order to prevent contamination of other pollen. After three days, pollen of the Chinese chive (flower ball) were coated on matured stigma of the onion. The flower was harvested three days after pollination. The flower was sterilized in a 75% ethanol solution for 1 minute and subsequently in 10% antiformin for 1 minute, and washed twice with sterile water. The ovule was then asceptically removed from the flower under microscope, placed on a medium and cultured at 25 T for 16 hours under the artificial light. The medium used was a solid medium prepared by adding 60 g/l of sucrose and 100 mg/l of inositol to an inorganic salt medium of Murashige & Skoog's medium and solidifying with agar. The hybrid embryo developed from the ovule was transplanted to the same medium as described above except for decreasing the concentration of sucrose to 20 g/l, and then cultured in the same manner. The hybrid embryo was acclimatized when it developed the second leaf and generated roots. The hybrid embryo was transplanted to a pot to grow into an adult hybrid plant.

Figure 5:
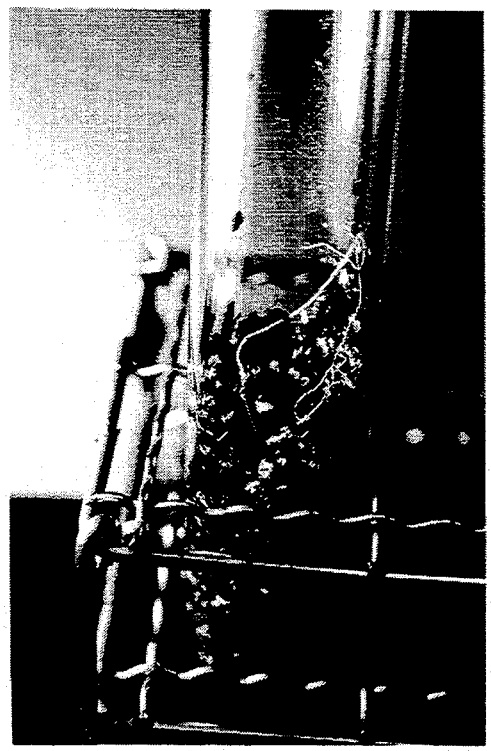
FIG. 5 illustrates that the hybrid plant obtained by hybridizing an onion and a Chinese chive developed the second foliage leaf and was acclimatized.

FIG. 5 shows the hybrid plant developed the second foliage leaf and was acclimatized.

The nature of the hybrid plant was tested as follows. The leaf shape and leaf arrangement of the hybrid plant were those of the Chinese chive. According to the constitution analysis as described in Example 1, the flavor precursors of the hybrid plant contained those of both the onion and the Chinese chive. The number of the chromosome was determined in the same manner as in Example 1 and found that the hybrid plant contained 24 chromosomes. The adult onion contains 16 chromosomes and its egg cell (female gamete) contains 8 chromosomes, while the adult Chinese chive contains 32 chromosomes (tetraploid) and its pollen (male gamete) contains 16 chromosomes. Accordingly, it was evident that the hybrid plant was a product of the crossbreeding of the egg cell of the onion with pollen of the Chinese chive.

EXAMPLE 3

Propagation of Hybrid Plants by Vegetative Propagation

Figure 6:
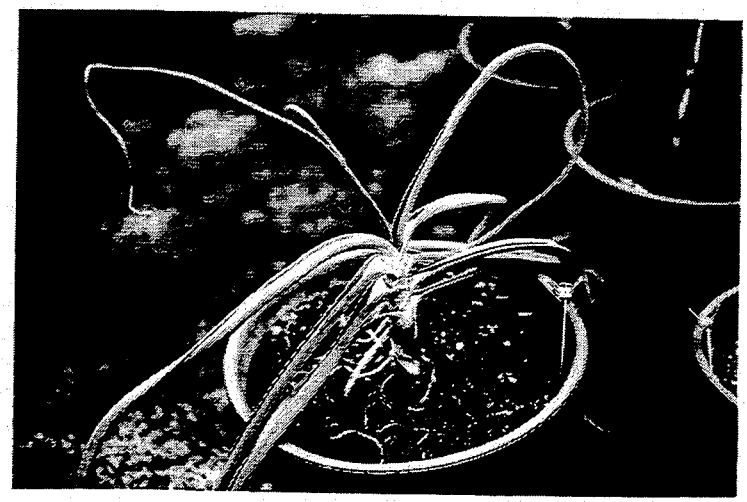
FIG. 6 illustrates the growth of leaves developed from cloves (of bulbs) of the hybrid plant of an onion and garlic.

The hybrid plant obtained in Example 1 formed a bulb in the summer. In October, the cloves of the bulb were disinfected by immersing in a 1,000-fold dilution of Benlate wettable powders for 30 minutes and then planted in a nursery garden which was previously tilled and applied with fertilizers. The top dressing was applied to the spaces between the rows at first in the beginning of February and then in April. The amounts of fertilizers applied are shown in Table 2. In order to protect the cloves from diseases and insect pests, Ortran and Sumithion were applied from the middle of April. The growth of the leaves became fast from March to May (see FIG. 6). The number of cloves which produced a bulb from the early summer to the midsummer was counted and found to be several to more than 10. Using cloves thus obtained, the same propagation was repeated.

TABLE 2

| | Amount of Fertilizer Applied (kg/10 are) | | |
|---|---|---|---|
| | Basal Fertilizer | First Topdressing | Second Topdressing |
| Compost | 1,200 | — | — |
| N (Nitrogen) | 7 | 6 | 6 |
| P (Phosphorous) | 12 | 5 | 5 |
| K (Potassium) | 5 | 5 | 5 |
| Magnesium lime | 100 | — | — |

EXAMPLE 4

Clonal Propagation of the Hybrid Plant

The growing points of the cloves of an onion × garlic hybrid plant were asceptically removed, placed on a medium and cultured. The medium used was prepared by adding 30 g/l of sucrose, 0.5 mg/l of nicotinic acid, 100 mg/l of inositol, 0.1 mg/l of thiamine hydrochloride, 0.5 mg/l of pyridoxal hydrochloride, 1 mg/l of glycine, and 0.5 mg/l of 1-naphthaleneacetic acid and 0.5 mg/l of 6-benzyladenine as plant growth regulators and 10 g/l of agar to a Murashige & Skoog's inorganic salt medium and adjusting to pH 5.8. The growing points were cultured at 25° C. for 16 hours under the artificial light to germinate microshoots. Almost all of the tissues produced multiple microshoots and formed multigerminated bodies. The multigerminated bodies were divided into individual microshoots which were then transplanted to a medium prepared by adding 30 g/l of sucrose, 0.5 mg/l of nicotinic acid, 100 mg/l of inositol, 0.1 mg/l of thiamine hydrochloride, 0.5 mg/l of pyridoxal hydrochloride, 1 mg/l of glycine, 0.1 mg/l of abscisic acid and 10 g/l of agar to a Murashige & Skoog's inorganic salt medium and adjusting to pH 5.8. The microshoots were cultured at 25° C. for 16 hours under the artificial light. After four weeks of culture, the juvenile plants with many shoots and roots were produced. The plants were acclimated for two weeks, and then potted. After the plants were grown in a greenhouse for approximately three weeks, they were transplanted to a field. The plantlets could be cultivated as described above in vegetative propagation for cloves and aerial bulbils.

DEPOSIT OF HYBRID CELLS

The hybrid cell DG-1 of an onion and a garlic was deposited with Fermentation Research Institute currently National Institute of Bioscience and Technology, Agency of Industrial Science and Technology 1-3, Higashi 1-chome, Tsukuba-shi, Ibaraki-ken 305, Japan under FERM BP-3164 (deposit date Nov. 17, 1990). A hybrid cell of an onion and a Chinese chive made according to the procedures described in Example 2 above was deposited with formerly Fermentation Research Institute, Agency of Industrial Science and Technology under FERM BD-4597 (deposit date Mar. 9, 1994.

The present invention is not to be limited in scope by the cells deposited since the deposit embodiments are intended as illustrations of one aspect of the invention and any cells which are functionally equivalent are within the scope of this invention. Indeed, various modifications of the invention in addition to these shown and described herein will become apparent to those skilled in the art from the foregoing description and accompanying drawings. Such modifications are intended to fall within the scope of the appended claims.

What is claimed is:

1. A hybrid cell of an onion and garlic or a hybrid cell of an onion and a Chinese chive, which is characterized by having totipotency including both embryogenic ability and differentiation potency and which is obtained by crossing an onion with either garlic or a Chinese chive by (a) fertilization of an onion with garlic pollen or of garlic with onion pollen or (b) fertilization of an onion with Chinese chive pollen or of Chinese chive with onion pollen, in which the hybrid cell is further characterized by genetic characteristics in the cytoplasm which are inherited exclusively from the maternal plant.

2. A hybrid embryo of an onion and garlic or of an onion and a Chinese chive which is characterized by having ability to germinate, differentiate and grow and which is obtained by culturing the hybrid cell according to claim 1 in a plant culture medium.

3. A hybrid secondary embryo of an onion and garlic or of an onion and a Chinese chive obtained by culturing the hybrid embryo according to claim 2 in a plant culture medium containing auxin or cytokinin.

4. A hybrid plant of an onion and garlic or of an onion and a Chinese chive obtained by regenerating the hybrid cell or culturing the hybrid embryo or the hybrid secondary embryo according to claims 1, 2 or 3.

5. A method for obtaining a hybrid embryo of an onion and garlic or a hybrid embryo of an onion and a Chinese chive, which comprises culturing a hybrid ovule obtained by crossing an onion with garlic or an onion with a Chinese chive by (a) fertilization of an onion with garlic pollen or of garlic with onion pollen or (b) fertilization of an onion with Chinese chive pollen or of Chinese chive with onion pollen, said hybrid embryo being capable of germinating, differentiating and growing.

6. A method for obtaining a hybrid plant of an onion and garlic or a hybrid plant of an onion and a Chinese chive, which comprises culturing a hybrid embryo obtained by the method according to claim 5.

7. A method for propagating a hybrid plant of an onion and garlic or an onion and a Chinese chive, which comprises cultivating a clove, an aerial bulbil or a seed of the hybrid plant.

8. A method for propagating a hybrid plant of an onion and garlic or of an onion and a Chinese chive, which comprises aseptically removing the growing point of a clove, a shoot or a root of said hybrid plant and culturing the hybrid growing point in a plant culture medium to effect clonal propagation of said hybrid plant.

9. A method for propagating a hybrid plant of an onion and garlic or of an onion and a Chinese chive, which comprises culturing the hybrid cell, the hybrid embryo or the hybrid secondary embryo according to claim 1, 2 or 3 in a plant culture medium to effect clonal propagation of said hybrid plant.

10. A method for obtaining a hybrid cell of an onion and garlic or a hybrid cell of an onion and a Chinese chive, which comprises (a) fertilizing an onion with garlic pollen or garlic with onion pollen or (b) fertilizing an onion with Chinese chive pollen or Chinese chive with onion pollen.

11. A method for obtaining a hybrid secondary embryo of an onion and garlic or of an onion and a Chinese chive by culturing the hybrid embryo obtained by the method according to claim 5 in a plant culture medium containing auxin or cytokinin.

* * * * *